United States Patent
Kellar et al.

(10) Patent No.: US 12,336,730 B2
(45) Date of Patent: Jun. 24, 2025

(54) SURGICAL CUTTING TOOL

(71) Applicant: ARTHREX, INC., Naples, FL (US)

(72) Inventors: Ryan A. Kellar, Naples, FL (US); Jerel Barrera, Seal Beach, CA (US); Sanjeev Kakar, Rochester, MN (US); Matthew Daggett, Leawood, KS (US); Claudine Reider, Ontario, CA (US); Bob Weber, Chino Hills, CA (US)

(73) Assignee: ARTHREX, INC., Naples, FL (US)

( * ) Notice: Subject to any disclaimer, the term of this patent is extended or adjusted under 35 U.S.C. 154(b) by 722 days.

(21) Appl. No.: 17/569,733

(22) Filed: Jan. 6, 2022

(65) Prior Publication Data
US 2022/0218379 A1    Jul. 14, 2022

Related U.S. Application Data

(60) Provisional application No. 63/136,595, filed on Jan. 12, 2021.

(51) Int. Cl.
*A61B 17/32* (2006.01)
*A61B 17/00* (2006.01)

(52) U.S. Cl.
CPC .......... *A61B 17/32002* (2013.01); *A61B 2017/00367* (2013.01); *A61B 2017/00438* (2013.01);
(Continued)

(58) Field of Classification Search
CPC ...... A61B 17/32002; A61B 17/320016; A61B 17/320783; A61B 2017/00367;
(Continued)

(56) References Cited

U.S. PATENT DOCUMENTS

| | | |
|---|---|---|
| 5,683,359 A | 11/1997 | Farkas et al. |
| 5,810,806 A | 9/1998 | Ritchart et al. |

(Continued)

FOREIGN PATENT DOCUMENTS

| | | |
|---|---|---|
| EP | 0605763 | 7/1994 |
| EP | 1156746 | 11/2001 |

(Continued)

OTHER PUBLICATIONS

International Search Report and Written Opinion, dated Mar. 24, 2022, pp. 1-18.

*Primary Examiner* — Ankit D Tejani
*Assistant Examiner* — Joshua Brendon Solomon
(74) *Attorney, Agent, or Firm* — ORBIT IP, LLP (57) ABSTRACT

A surgical cutting tool with a body having a proximal end and a distal end; a cannula rotatably extending from the distal end of the body, the cannula having a proximal end and a distal end; a cutting head removably coupled to the distal end of the cannula, the cutting head having a distal tip and a cutting window; a hollow shaft movably positioned inside the cannula, the hollow shaft having a blade; a suction connector in fluid communication with the hollow shaft, the suction connector being configured for connection to a suction source; a suction control configured to alter suction from the suction connector to the hollow shaft; and an actuator coupled to the hollow shaft for moving the blade of the hollow shaft relative to the cutting window of the cutting head.

22 Claims, 9 Drawing Sheets

(52) U.S. Cl.
CPC ............. *A61B 2017/320028* (2013.01); *A61B 2017/32004* (2013.01); *A61B 2017/320064* (2013.01); *A61B 2217/005* (2013.01)

(58) Field of Classification Search
CPC ......... A61B 2017/00438; A61B 2017/320028; A61B 2017/32004; A61B 2017/320064; A61B 2017/00473; A61B 2217/005
See application file for complete search history.

(56) References Cited

U.S. PATENT DOCUMENTS

| | | |
|---|---|---|
| 5,873,886 A | 2/1999 | Larsen et al. |
| 5,899,884 A | 5/1999 | Cover et al. |
| 6,620,180 B1 | 9/2003 | Bays et al. |
| 7,491,202 B2 | 2/2009 | Odom et al. |
| 7,708,756 B2 | 5/2010 | Nobis et al. |
| 7,789,825 B2 | 9/2010 | Nobis et al. |
| 7,794,393 B2 | 9/2010 | Larsen |
| 8,162,850 B2 | 4/2012 | Parihar et al. |
| 8,414,587 B2 | 4/2013 | Saal et al. |
| 8,486,097 B2 | 7/2013 | Mark et al. |
| 9,398,920 B2 | 7/2016 | Doll et al. |
| 9,585,675 B1 | 3/2017 | Germain et al. |
| 10,034,684 B2 | 7/2018 | Weisenburgh, II et al. |
| 10,285,731 B2 | 5/2019 | Adams et al. |
| 10,617,438 B2 | 4/2020 | O'Keefe et al. |
| 10,667,839 B2 | 6/2020 | Chin |
| 2004/0153111 A1 | 8/2004 | Hosoada |
| 2009/0124975 A1* | 5/2009 | Oliver ............... A61B 17/32002 606/167 |
| 2017/0296199 A1* | 10/2017 | Beger ................ A61B 17/1611 |

FOREIGN PATENT DOCUMENTS

| | | |
|---|---|---|
| EP | 1518492 | 3/2005 |
| EP | 1518500 | 3/2005 |
| EP | 1610695 | 1/2006 |
| EP | 2114266 | 11/2009 |
| EP | 2156796 | 2/2010 |
| EP | 2227154 | 3/2017 |
| EP | 3524188 | 8/2019 |
| EP | 3590449 | 1/2020 |
| WO | 2009064688 | 5/2009 |
| WO | 2016204997 | 12/2016 |
| WO | 2019210004 | 10/2019 |

* cited by examiner

SURGICAL CUTTING TOOL

CROSS REFERENCE TO RELATED APPLICATION

This application claims priority of U.S. Provisional Patent Application No. 63/136,595, filed on Jan. 12, 2021, entitled SURGICAL CUTTING TOOL, the entire contents of which are hereby incorporated herein by reference.

BACKGROUND

The present disclosure relates to devices used in endoscopic surgery and, more particularly, to a tissue cutting tool with suction.

There is a need for a surgical cutting tool that remedies the shortcomings of prior art surgical cutting tools.

SUMMARY

The present disclosure relates to improved tissue cutting tools. A surgical cutting tool, according to an implementation has: a body with a proximal end and a distal end; a cannula rotatably extending from the distal end of the body, the cannula having a proximal end and a distal end; a cutting head removably coupled to the distal end of the cannula, the cutting head having a distal tip and a cutting window; a hollow shaft movably positioned inside the cannula, the hollow shaft having a blade; a suction connector in fluid communication with the hollow shaft, the suction connector being configured for connection to a suction source; a suction control configured to alter suction from the suction connector to the hollow shaft; and an actuator coupled to the hollow shaft for moving the blade of the hollow shaft relative to the cutting window of the cutting head.

In an implementation, the surgical cutting tool has a plurality of interchangeable cutting heads. Optionally, at least one of the plurality of interchangeable cutting heads has a rounded distal end. At least one of the plurality of interchangeable cutting heads may have a rounded distal end and a cutting window oriented at an angle pointing away from the rounded distal end. Optionally, at least one of the plurality of interchangeable cutting heads has an angled distal end. At least one of the plurality of interchangeable cutting heads may have an angled distal end and a cutting window oriented at an angle pointing toward the angled distal end.

Optionally, at least one of the plurality of interchangeable cutting heads has a flat distal end and a cutting window positioned proximal to the flat distal end. At least one of the plurality of interchangeable cutting heads may have an angled distal end that extends beyond a diameter of the cannula and a cutting window positioned proximal to the angled distal end.

In an implementation, the suction control is coupled to the body and movable between an open position to reduce suction through the hollow shaft and the cutting window and a closed position to increase suction through the hollow shaft and the cutting window. The suction control may have a crenelated surface. In an implementation, the body has a handle with a thumb loop; and the actuator has a finger loop.

In an additional implementation, a surgical cutting tool has a body with a distal end; a handle positioned proximal to the distal end; a suction connector, the suction connector being configured for connection to a suction source; a suction pathway extending from the suction connector through at least a portion of the body; and a control pathway in fluid communication with the suction pathway. A cannula rotatably extends from the distal end of the body, the cannula having a proximal end and a distal end. A cutting head is removably coupled to the distal end of the cannula, the cutting head having a distal tip and a cutting window. A hollow shaft is movably positioned inside the cannula, the hollow shaft having a blade. A suction control is slidably coupled to the body and configured to adjustably open the control pathway to alter suction from the suction connector to the hollow shaft. An actuator is rotatably coupled to the body and coupled to the hollow shaft for moving the blade of the hollow shaft relative to the cutting window of the cutting head. In an implementation, the handle has a thumb loop; the actuator has a finger loop; and the handle and actuator are operated as a scissors to move the shaft.

According to an implementation, the surgical cutting tool may be used by inserting the cannula into a patient to a desired surgical site; orienting the cutting window to the tissue to be cut; manipulating the actuator to move the shaft blade across the cutting window to sever tissue extending into the cutting window; and withdrawing the cannula from a patient. Optionally, prior to insertion, the suction control is moved to an open position to reduce suction through the hollow shaft and the cutting window. Optionally, after inserting the cannula into a patient, the suction control is moved to a closed position to increase suction through the hollow shaft and the cutting window to draw tissue into the cutting window.

These and other features are described below.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred implementations, reference is made to the accompanying drawings which show by way of illustration specific implementations in which the invention may be practiced. Wherever possible, the same reference numbers will be used throughout the drawings to refer to the same or like parts. It is to be understood that other implementations may be utilized and structural and functional changes may be made without departing from the scope of this disclosure.

With reference to FIGS. 1 to 7, a surgical cutting tool 10 according to an implementation has a body 12. The body 12 has a proximal end 14 and a distal end 16. A cannula 18 is coupled to the distal end 16 of the body 12. The cannula 18 has a proximal end 20 and a distal end 22. A cutting head 24 is coupled to the distal end 22 of the cannula 18. The cannula 18 length may be varied depending on the desired application. In an implementation, the cannula 18 has a length of between about 50 mm and about 150 mm. In an implementation, the cannula 18 has a length of about 70 mm. In an implementation, the cannula 18 has a length of about 130 mm.

The body 12 has a handle 26. In an implementation, the handle has a loop 28 for placement of a user's finger, such as a thumb. An actuator 30 is coupled to the body 12. In an implementation, the actuator 30 has a loop 32 for placement of a user's finger, such as a forefinger. The actuator 30 is rotatably mounted to the housing such as by using a pin 34. The thumb of a user may be placed in the handle loop 28 and the forefinger in the actuator loop 32 and the handle 26 and the actuator 30 manipulated as a scissors. Optionally, in an implementation, a spring is mounted between the handle 26 and the actuator 30 to maintain the actuator in a predetermined position relative to the handle.

Figure 1:
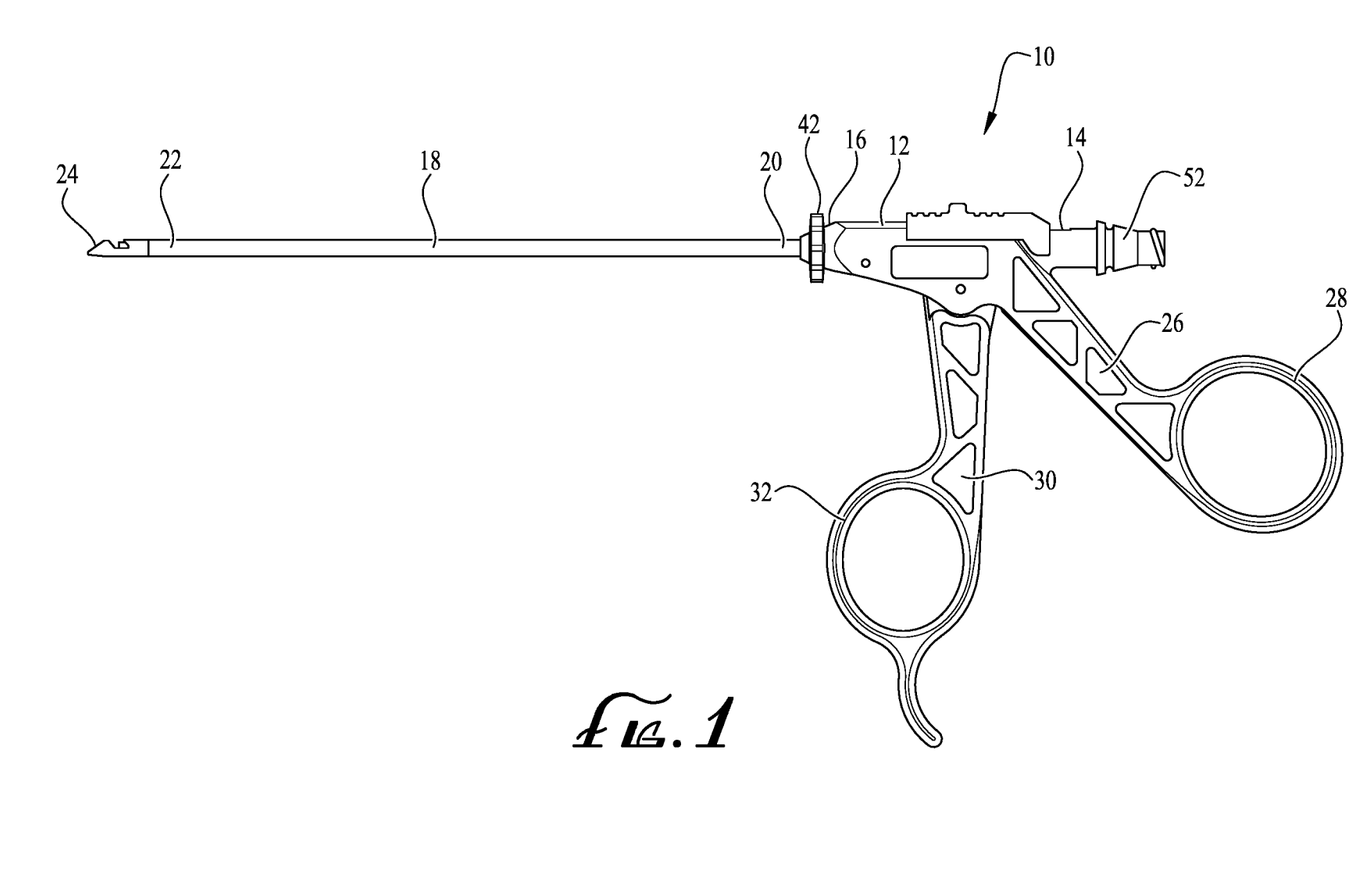
FIG. 1 is a side elevation view of a surgical cutting tool according to an implementation.
Figure 2:
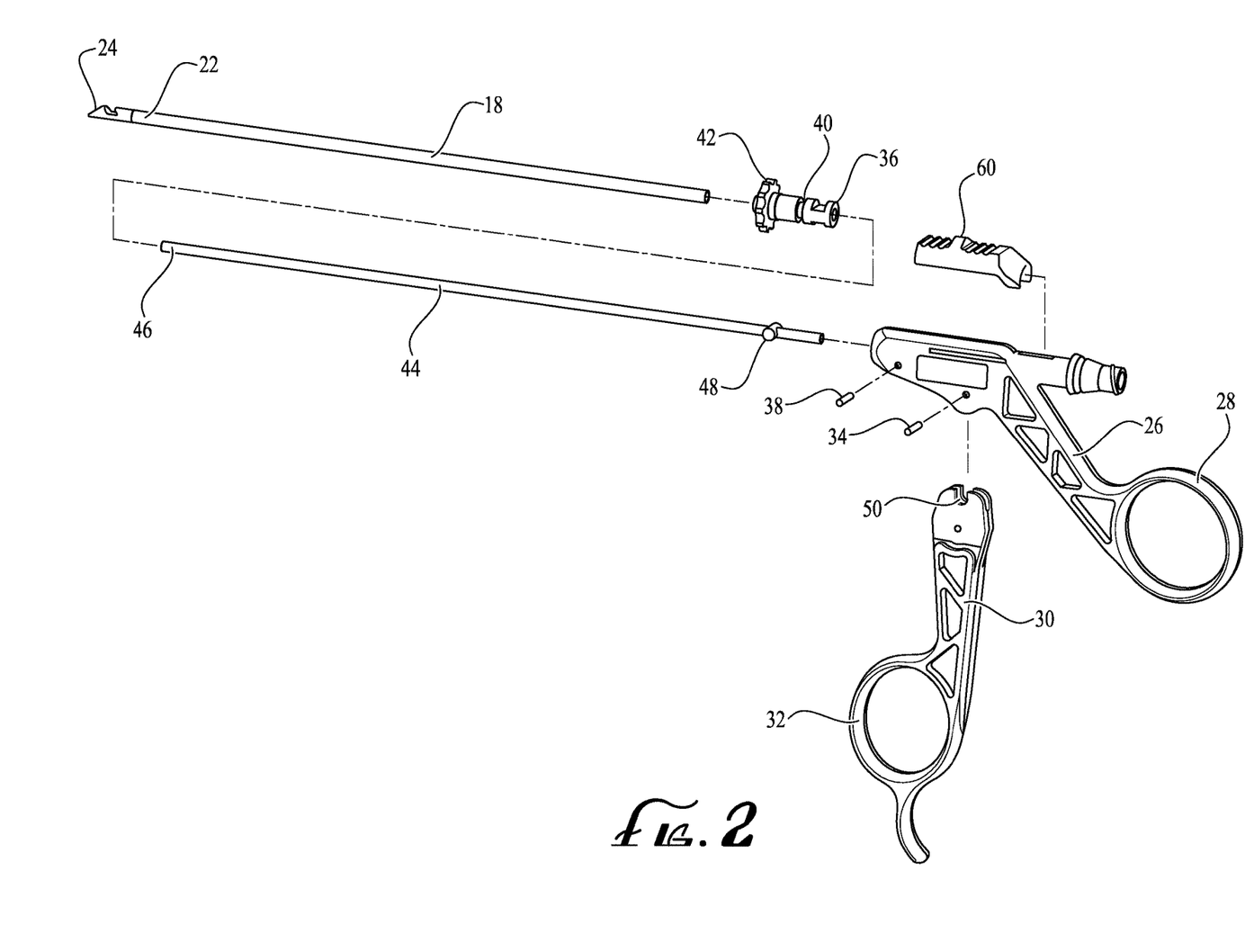
FIG. 2 is an exploded side elevation cross-sectional view of the surgical cutting tool of FIG. 1.
Figure 3:
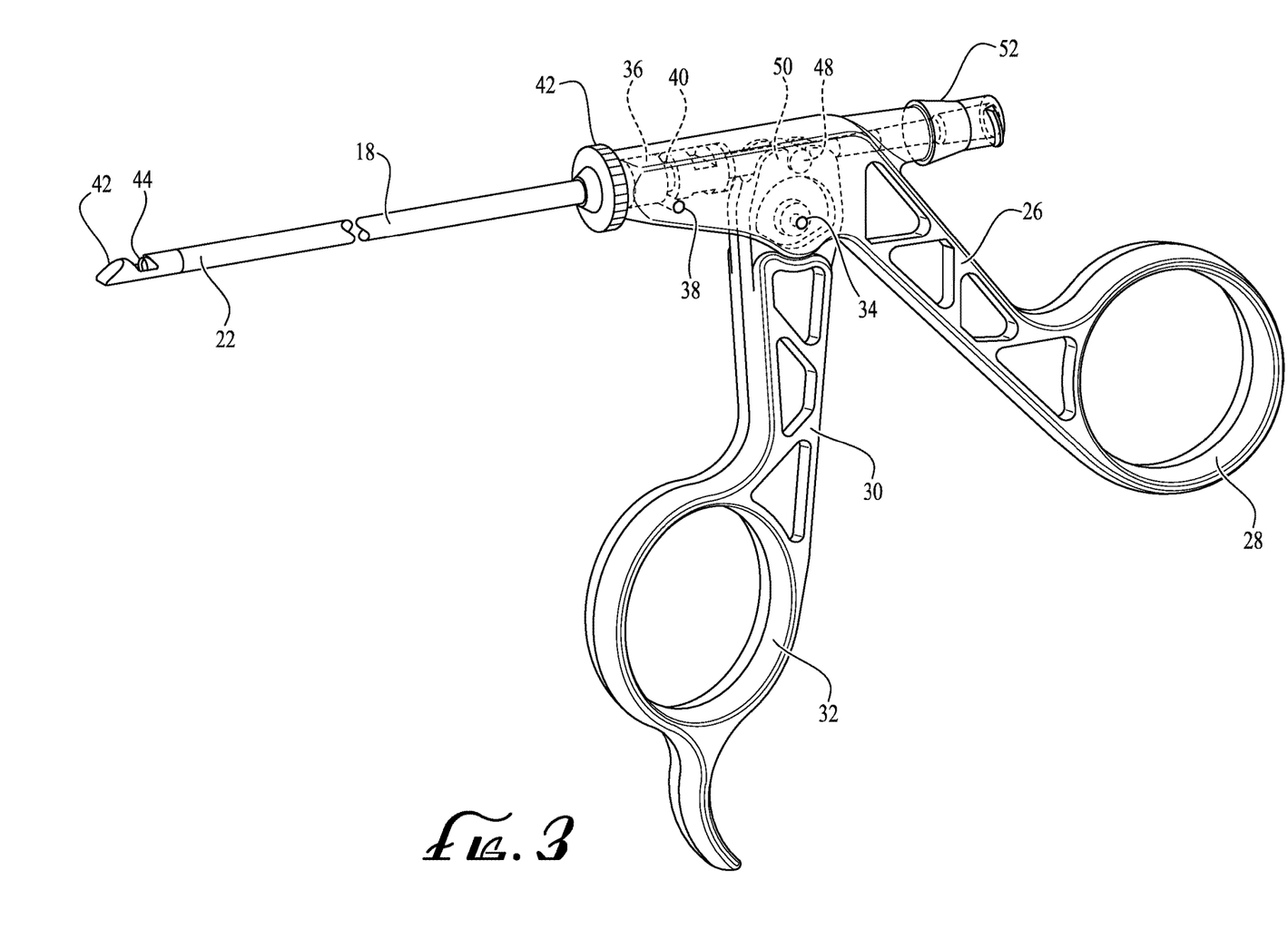
FIG. 3 is a perspective elevation view of a surgical cutting tool according to an implementation with a portion of the housing shown as semi-transparent.
Figure 4:
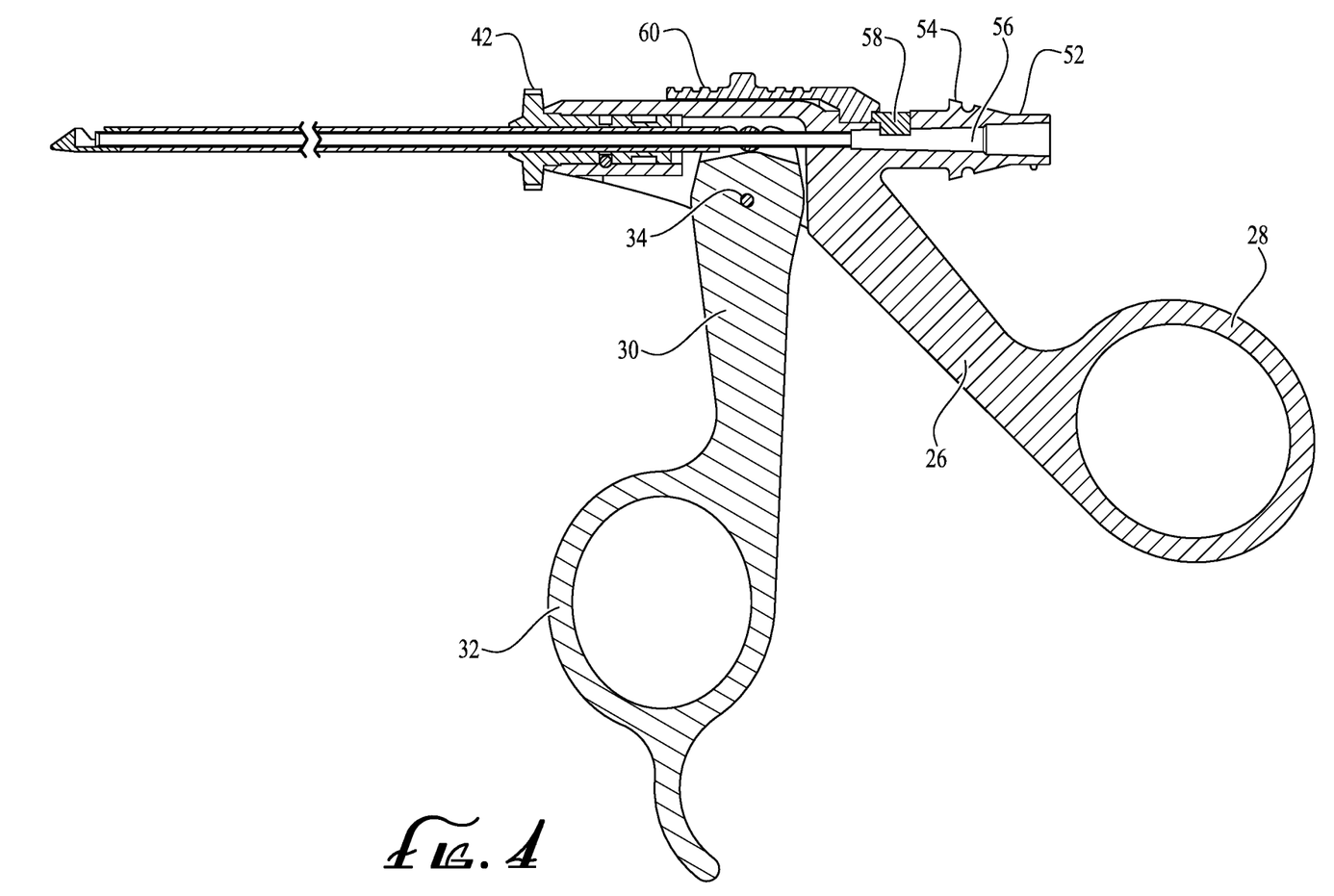
FIG. 4 is a side elevation cross-sectional view of a surgical cutting tool according to an implementation.

The proximal end 20 of the cannula 18 is coupled to a rotating hub 36. In an implementation, the rotating hub 36 is welded onto an outside surface of the cannula 18. The body 12 is configured so that the rotating hub 36 fits inside of a hub opening. A pin 38 extends through the body 12 and rests in a groove 40 of the rotating hub 36 to prevent axial movement, but to allow rotation, of the hub and the cannula 18. The groove 40 may extend entirely around the rotating hub 36 to allow for 360 degree rotation of the hub and the cannula 18. Alternatively, the groove 40 may extend less than entirely around the rotating hub 36 if it is desired to limit rotation of the rotating hub and the cannula 18.

The rotating hub 36 allows the cannula 18 to be rotated so the cutting head 24 orientation can change as explained in more detail below. In an implementation, the rotating hub 36 has a knob 42 to assist a user in rotating the cannula 18. In an implementation, the knob 42 is crenelated or otherwise textured to assist a user in locating and turning the knob.

Positioned inside of the cannula 18 and extending into the body 12 is a hollow shaft 44. The hollow shaft 44 has a blade 46 which cooperates with cutting head 24 as further explained below. The shaft 44 is coupled to the actuator 30. In an implementation, a cross pin 48 is coupled to the shaft 44. The cross pin 48 may be welded to the shaft 44. The cross pin 48 rests in a groove 50 on the actuator 30. As the actuator 30 is rotated relative to the body 12, the groove 50 moves the cross pin 48 and with it the shaft 44. The shaft 44 and the blade 46 may be made from stainless steel and the blade 46 may be made of a different material than the rest of the shaft. Additionally, the blade 46 may be removably attached to the shaft 44. The shaft 44 moves linearly within the cannula 18 to cut tissue positioned in the cutting head 24 as explained in more detail below.

The body 12 also has a suction port 52 for connection of a suction source (not shown). The suction port may have a barb 54 or threads for retaining a suction source connector. In an implementation, the suction port 52 is positioned on the proximal end 14 of the body 12. As shown in FIG. 4, the suction port 52 is in fluid communication with a suction pathway 56 through the body 12 and to the shaft 44. Additionally, the suction port 52 is in fluid communication with a control pathway 58. A suction control 60 is movably positioned on the body.

Figure 5:
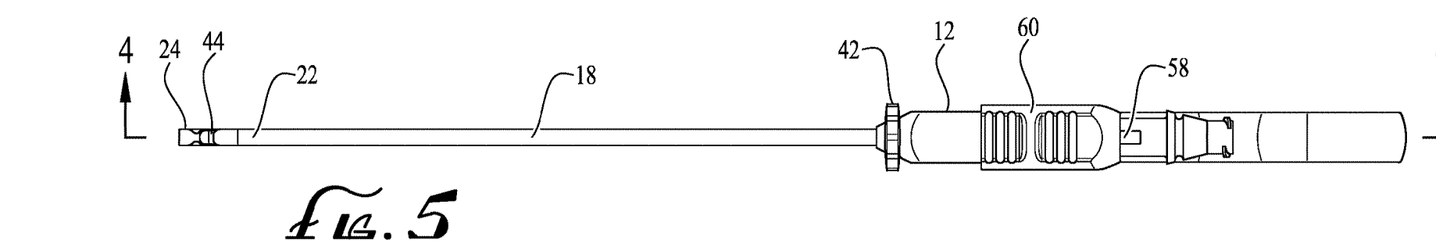
FIG. 5 is a top view of a surgical cutting tool according to an implementation with a suction control in a open position.
Figure 6:
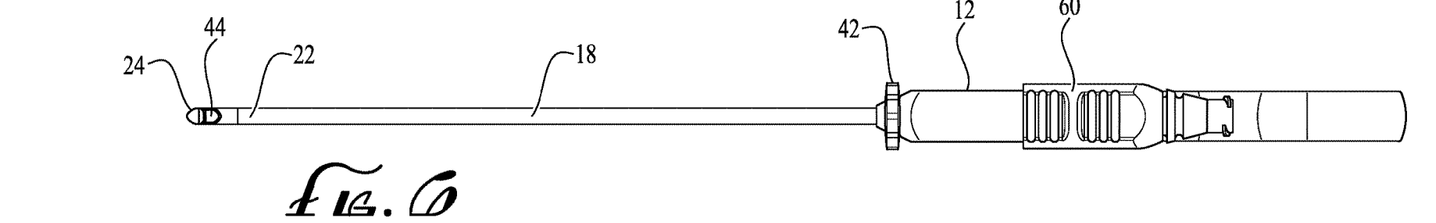
FIG. 6 is a top view of a surgical cutting tool according to an implementation with a suction control in a closed position.

In an implementation, the suction control 60 is slidably movable between an open position and a closed position. In the open position, air may be pulled into the body 12 through the control pathway 58 rather than through the cutting head 24 and the shaft 44. In the closed position, the suction pulls air in through cutting head 24 and the shaft 44. The user may move the suction control 60 between the open and closed positions to vary the amount of suction at the cutting head 24. The suction control 60 may be crenelated or otherwise textured to assist a user in locating and manipulated the suction control.

Figure 7:
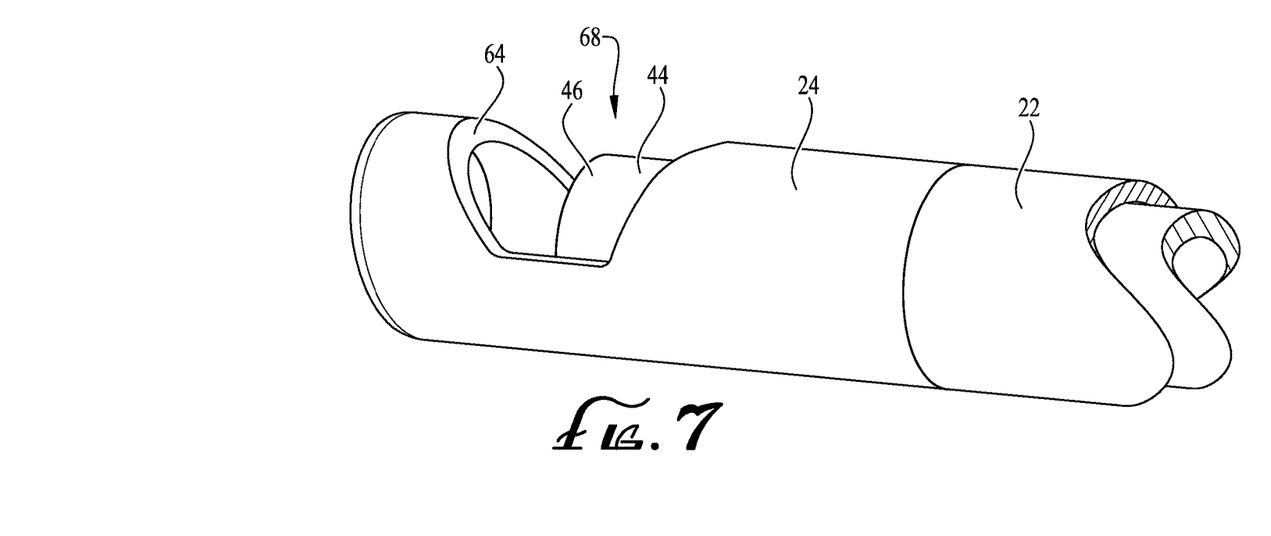
FIG. 7 is an enlarged view of a portion of a cannula, shaft and cutting head according to an implementation.

The cutting head 24 may be varied for different applications. In an implementation, the cutting head 24 is removably coupled to the distal end 22 of the cannula 18, such as by mating threads. Alternatively, the surgical cutting tool 10 may be configured with a specific cutting head 24. As shown in FIG. 7, the cutting head 34 has a cutting window 62 with a cutting edge 64. As the shaft 44 is advanced through the cannula 18, the blade 46 of the shaft passes along the cutting edge 64 and severs any tissue extending into the cutting window 62. In an implementation, the blade 46 is circular so that the blade 46 can cut tissue regardless of the orientation of the cutting head 24 and the cutting window 62.

Suction may assist in pulling tissue into the cutting window 62. Additionally, suction may assist in removing cut tissue from the cutting window 62 by pulling the cut tissue back through the shaft 44, through the suction pathway 56 and out through the suction port 52. In an implementation, a tissue capture container is placed between the suction source and the suction port 52 to catch cut tissue. In an additional implementation, liquid or pressurized gas may be communicated into the suction port 52 and out through the cutting window 62.

Figures 8A, 8B:
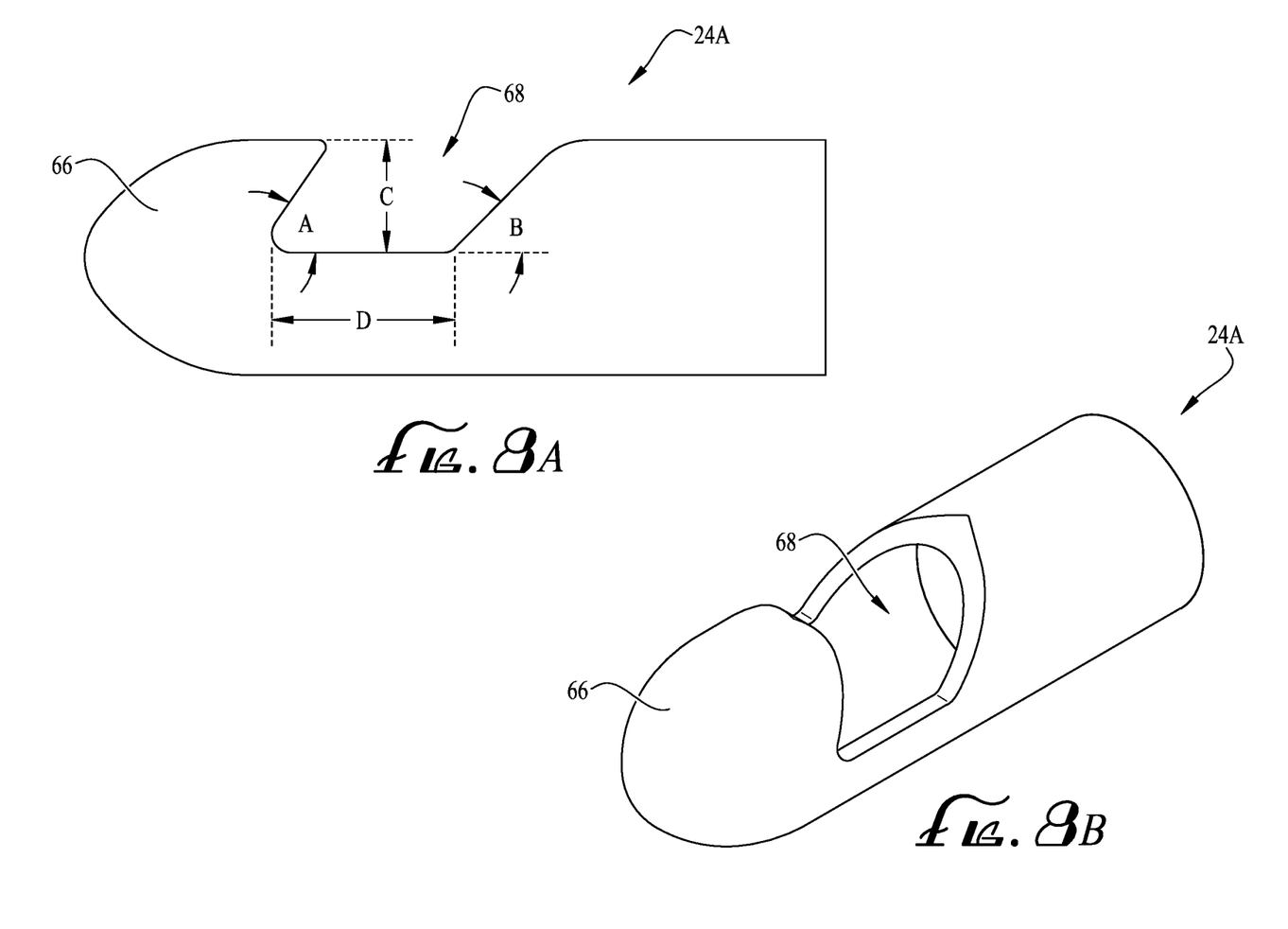
FIG. 8A is a side elevation view of a cutting head for a surgical cutting tool according to an implementation.
FIG. 8B is a perspective elevation view of the cutting head of FIG. 8A.

Cutting heads according to several implementations are described below. The implementations are intended to be illustrative and not restrictive. As shown in FIGS. 8A and 8B, the cutting head 24A, according to an implementation, may have a diameter of about 3 mm and may be formed with a rounded distal end 66. The rounded distal end 66 may be helpful for pushing the surgical cutting tool 10 through tissue to reach a surgical site. Positioned proximal to the distal end 66 is a cutting window 68. The cutting window 68 may be oriented at an angle pointing away from the distal end 66. The cutting window has a distal wall and proximal wall separated by a flat central portion. In an implementation, the distal wall has an angle A of from about 40 degrees to about 70 degrees, and more preferably about 55 degrees. In an implementation, the proximal wall has an angle B of from about 30 degrees to about 60 degrees, and more preferably about 45 degrees. In an implementation, the cutting window 68 has a depth C of from about 0.03 inches to about 0.09 inches, and more preferably about 0.06 inches. In an implementation, the cutting window 68 has a length D of from about 0.05 inches to about 0.15 inches, and more preferably about 0.10 inches.

In use, cutting head 24A operates like a hook and a user moves the distal end 66 past the tissue to be cut and then pulls the cutting head backward (with or without suction) to lead tissue into the cutting window 68. The actuator 30 is then manipulated by the user to move the shaft 44 distally with the blade 46 of the shaft moving across the cutting window 68 to cut whatever tissue is in the cutting window. The cutting head 24A may be useful for hand and wrist, ENT (ear, nose and throat), Spine and other arthroscopic surgery applications. The back biter distal tip design allows surgeons the ability to use standard portals and efficiently resect soft tissue such as the TFCC (triangular fibrocartilage complex) in a retrograde distal to proximal direction.

Figures 9A, 9B:
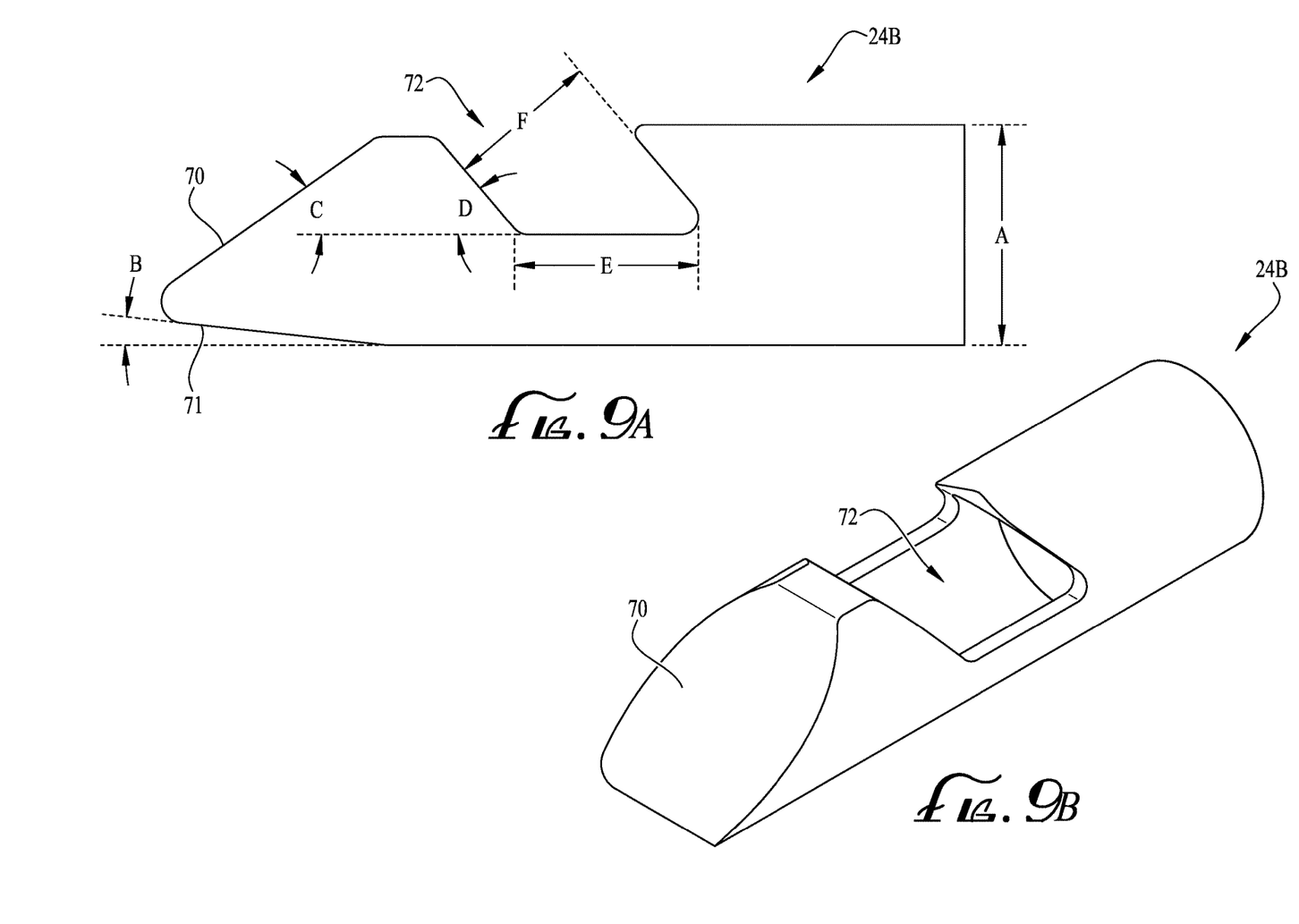
FIG. 9A is a side elevation view of a cutting head for a surgical cutting tool according to an additional implementation.
FIG. 9B is a perspective elevation view of the cutting head of FIG. 9A.

As shown in FIGS. 9A and 9B, the cutting head 24B may have a diameter A of about 3 mm and an angled distal end 70. The angled distal end may have an undercut edge 71 with angle B of from about 0 degrees to about 15 degrees and more preferably about 6 degrees. The remainder of the angled distal end 70 may be at an angle C of from about 20 degrees to about 50 degrees and more preferably about 35 degrees. The angled distal end 70 may be helpful in lifting tissue or in maneuvering the cutting head 34B between two closely positioned structures.

Positioned about 0.05 inches to about 0.15 inches, and more preferably about 0.11 inches proximal to the distal end 70 is a cutting window 72. The cutting window 72 may be oriented at angle pointing toward the distal end 70. In an implementation, the cutting window is oriented at an angle D of from about 35 degrees to about 65 degrees and more preferably about 50 degrees. The cutting window 72 has angled distal and proximal walls separated by a flat central portion. In an implementation, the flat central portion has a length E of from about 0.05 inches to about 0.15 inches, and more preferably about 0.10 inches. In an implementation, the distal wall and proximal wall are separated by a distance F of from about 0.04 inches to about 0.12 inches, and more preferably about 0.08 inches.

In use, cutting head 34B operates like a scoop or sled and a user moves the distal end 70 to the tissue to be cut and then scoops the tissue into the cutting window 72 with or without suction. The actuator 30 is then manipulated by the user to move the shaft 44 distally with the blade 46 of the shaft moving across the cutting window 72 to cut whatever tissue is in the cutting window. The cutting head 24B may be useful for knee surgery applications, such as for cutting and manipulating edges of meniscal tissue and other hard to reach flat tissue pathologies in various arthroscopic and endoscopic surgical applications.

Figures 10A, 10B:
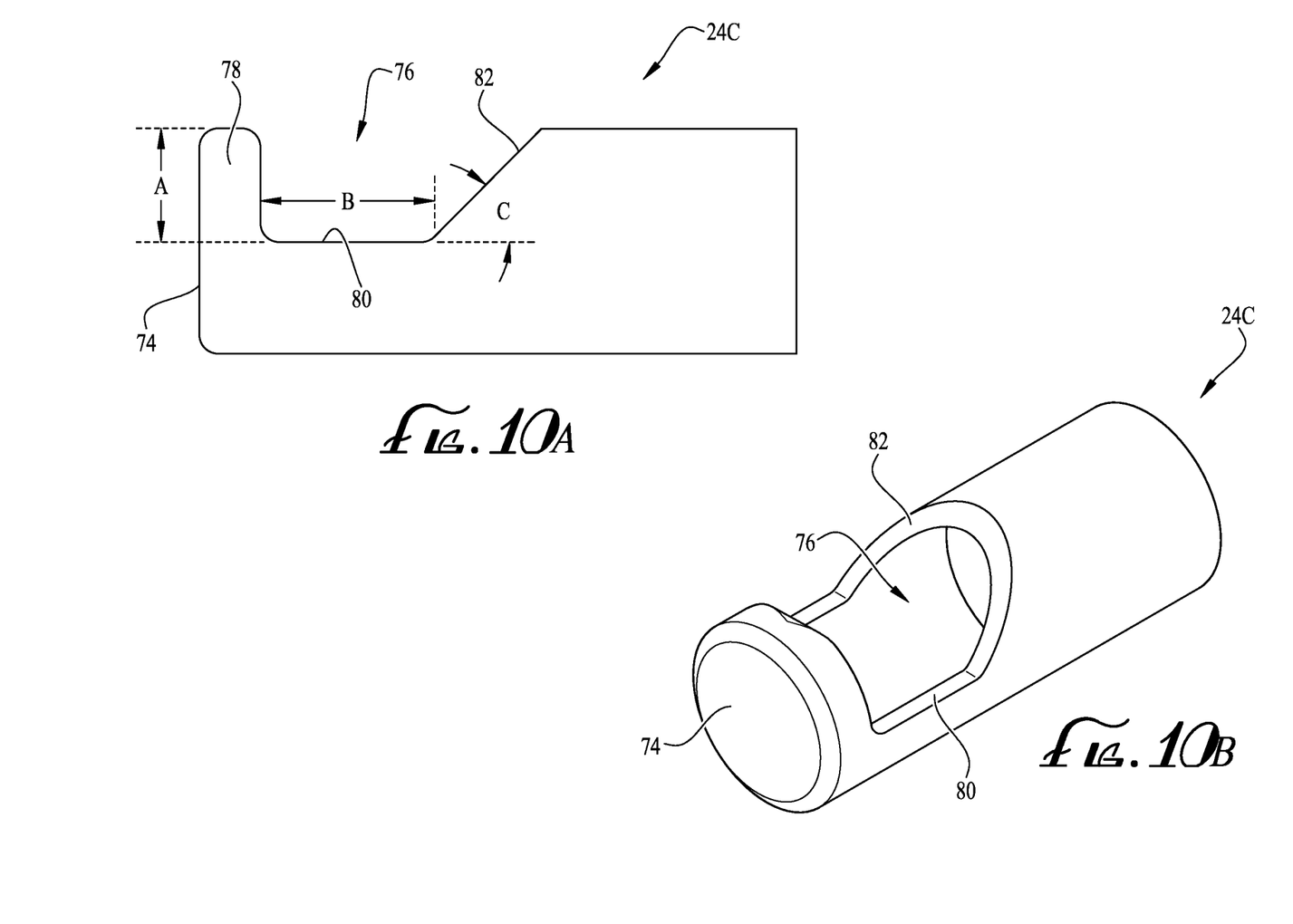
FIG. 10A is a side elevation view of a cutting head for a surgical cutting tool according to an additional implementation.
FIG. 10B is a perspective elevation view of the cutting head of FIG. 10A.

As shown in FIGS. 10A and 10B, the cutting head 24C may be formed with a diameter of about 3 mm and with a flat distal end 74. The flat distal end 74 may be helpful in pushing tissue out of the way of the cutting tool and establishing a clear edge for cutting. Positioned proximal to the distal end 74 is a cutting window 76. The cutting window 76 may be oriented have a flat distal wall 78 that transitions to a flat inner edge 80 perpendicular to the flat distal wall. The flat inner edge 80 may transition to a proximally angled edge 82 (extending outwardly as the edge extends proximally). The flat distal wall 78 may have a height A from about 0.05 inches to about 0.15 inches, and more preferably about 0.10 inches. The flat inner edge 80 may have a length B of from about 0.03 inches to about 0.10 inches, and more preferably about 0.06 inches. The proximally angled edge 82 may extend at an angle C of from about 30 degrees to about 60 degrees, and more preferably about 45 degrees.

In use, a user moves the distal end 78 proximal to the tissue to be cut and then activates suction to pull the tissue into the cutting window 76. The actuator 30 is then manipulated by the user to move the shaft 44 distally with the blade 46 of the shaft moving across the cutting window 76 to cut whatever tissue is in the cutting window. The cutting head 24C allows surgeons a more traditional cutting method for procedures, such as, for example, meniscectomies and soft-tissue debridement and removal.

Figures 11A, 11B:
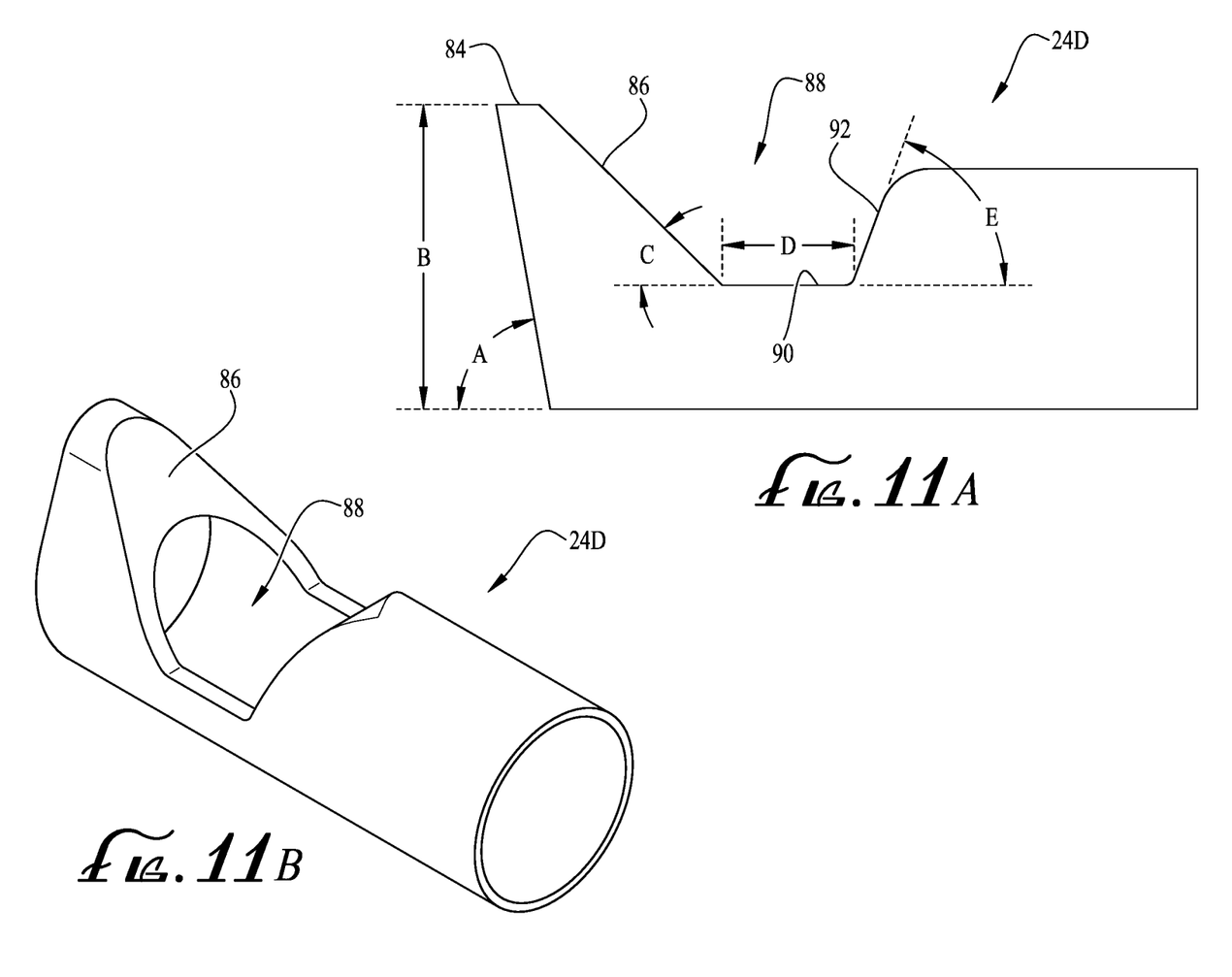
FIG. 11A is a side elevation view of a cutting head for a surgical cutting tool according to an additional implementation.
FIG. 11B is a perspective elevation view of the cutting head of FIG. 11A.

As shown in FIGS. 11A and 11B, the cutting head 24D may be formed with a distally angled distal end 84 that extends beyond a diameter of the cannula 18. In an implementation, the distally angled edge has an angle A of from about 65 degrees to about 95 degrees, and more preferably about 80 degrees. The distally angled edge may have a height B of from about 0.10 inches to about 0.20 inches, and more preferably about 0.15 inches. The distally extending sloped end 84 may be helpful in lifting tissue or in maneuvering the cutting head between closely positioned structures.

A proximal surface 86 of the sloped end 84 may form a distal wall of a cutting window 88. In an implementation, the proximal surface 86 has an angle C of from about 30 degrees to about 60 degrees, and more preferably about 45 degrees. The proximal surface 86 of the sloped end 84 transitions to a flat inner edge 90 parallel to a longitudinal axis. In an implementation, the flat inner edge has a length D of from about 0.02 inches to about 0.10 inches, and more preferably about 0.06 inches. The flat inner edge 90 may transition to a proximally angled edge 92 (extending outwardly as the edge extends proximally). In an implementation, the inner edge 90 has an angle E of from about 55 degrees to about 85 degrees, and more preferably about 70 degrees.

In use, a user moves the sloped end 84 past the portion to be cut and then activates suction to pull tissue into the cutting window 88. The actuator 30 is then manipulated by the user to move the shaft 44 distally with the blade 46 of the shaft moving across the cutting window 88 to cut whatever tissue is in the cutting window. This cutting head 24D design allows for safe and efficient removal of bone and tissue, such as, for example, laminectomy within the spine without the need to remove the instrument from the spinal canal. The suction port eliminates the need of the surgeon to manually remove tissue and bone after each cut.

Use of the cutter, according to implementations, will now be described. With the suction control 58 in a closed position, the cannula 18 of the surgical cutting tool 10 is inserted into a patient. During insertion, the actuator 30 may be used to position the shaft 44 to cover the cutting window 72 to prevent tissue from entering the cutting window. Once at the desired location, movement of the cannula 18 is ceased. If desired, a user may rotate the cannula 18 using the knob 42 to change the orientation of the cutting head 24. If desired, a user may also move the suction control 58 to variably position tissue within the cutting window 62 of the cutting head 24. Once the tissue to be cut is positioned within the cutting window 62, the user may manipulate the actuator 30 to move the shaft blade 46 across the cutting window 62 to cut the tissue. After the tissue has been cut, the user may release the actuator 30 and repeat the process to conduct additional cutting, or remove the cannula 18 from the patient.

The surgical cutting tool may be used, for example, in traditional and small joint arthroscopy and endoscopy. The surgical cutting tool may be used within a dry arthroscopic procedures without overheating concerns. Additionally, the surgical cutting tool may be used in standard arthroscopy with in-flow. Variable suction control allows the surgical cutting tool to be used in a broad variety of surgical procedures. Interchangeable cutting heads allow for the surgical cutting tool to be used in a broad variety of surgical procedures without the need for separate instruments. Additionally, the scissor grip and suction control allow for versatile single-handed operation. In an implementation, the handles 26, 30 and suction control 60 are made from Radel and the remaining components are made from stainless steel.

There is disclosed in the above description and the drawings, a surgical cutting tool and method that fully and effectively overcomes the disadvantages associated with the prior art. However, it will be apparent that variations and modifications of the disclosed implementations may be made without departing from the principles of the invention. The presentation of the implementations herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. A surgical cutting tool comprising:
    a body further comprising a proximal end and a distal end;
    a cannula rotatably extending from the distal end of the body, the cannula further comprising a proximal end and a distal end;
    a cutting head removably coupled to the distal end of the cannula, the cutting head further comprising a distal tip and a cutting window;
    a hollow shaft movably positioned inside the cannula, the hollow shaft further comprising a blade;
    a suction connector in fluid communication with the hollow shaft, the suction connector being configured for connection to a suction source;
    a suction control configured to alter suction from the suction connector to the hollow shaft; and
    an actuator coupled to the hollow shaft for moving the blade of the hollow shaft relative to the cutting window of the cutting head;
    wherein the suction control is coupled to the body and movable between an open position to reduce suction through the hollow shaft and the cutting window and a closed position to increase suction through the hollow shaft and the cutting window.

2. The surgical cutting tool of claim 1 further comprising a plurality of interchangeable cutting heads.

3. The surgical cutting tool of claim 2 wherein at least one of the plurality of interchangeable cutting heads further comprises a rounded distal end.

4. The surgical cutting tool of claim 3 wherein at least one of the plurality of interchangeable cutting heads further comprises a rounded distal end and a cutting window oriented at an angle pointing away from the rounded distal end.

5. The surgical cutting tool of claim 3 wherein at least one of the plurality of interchangeable cutting heads further comprises an angled distal end.

6. The surgical cutting tool of claim 3 wherein at least one of the plurality of interchangeable cutting heads further comprises an angled distal end and a cutting window oriented at an angle pointing toward the angled distal end.

7. The surgical cutting tool of claim 3 wherein at least one of the plurality of interchangeable cutting heads further comprises a flat distal end and a cutting window positioned proximal to the flat distal end.

8. The surgical cutting tool of claim 3 wherein at least one of the plurality of interchangeable cutting heads further comprises an angled distal end that extends beyond a diameter of the cannula and a cutting window positioned proximal to the angled distal end.

9. The surgical cutting tool of claim 1 wherein the suction control has a crenelated surface.

10. The surgical cutting tool of claim 1 wherein the body further comprises a handle with a thumb loop; and the actuator further comprises a finger loop.

11. A surgical cutting tool comprising:
    a body further comprising
        a distal end;
        a handle positioned proximal to the distal end;
        a suction connector, the suction connector being configured for connection to a suction source;
        a suction pathway extending from the suction connector through at least a portion of the body; and
        a control pathway in fluid communication with the suction pathway;
    a cannula rotatably extending from the distal end of the body, the cannula having a proximal end and a distal end;
    a cutting head removably coupled to the distal end of the cannula, the cutting head further comprising a distal tip and a cutting window;
    a hollow shaft movably positioned inside the cannula, the hollow shaft further comprising a blade;
    a suction control slidably coupled to the body and configured to adjustably open the control pathway to alter suction from the suction connector to the hollow shaft; and
    an actuator rotatably coupled to the body and coupled to the hollow shaft for moving the blade of the hollow shaft relative to the cutting window of the cutting head.

12. The surgical cutting tool of claim 11 wherein the handle further comprises a thumb loop; the actuator further comprises a finger loop; and wherein the handle and actuator are operated as a scissors to move the shaft.

13. The surgical cutting tool of claim 11 further comprising a plurality of interchangeable cutting heads.

14. The surgical cutting tool of claim 13 wherein at least one of the plurality of interchangeable cutting heads further comprises a rounded distal end.

15. The surgical cutting tool of claim 13 wherein at least one of the plurality of interchangeable cutting heads further comprises a rounded distal end and a cutting window oriented at an angle pointing away from the rounded distal end.

16. The surgical cutting tool of claim 13 wherein at least one of the plurality of interchangeable cutting heads further comprises an angled distal end.

17. The surgical cutting tool of claim 13 wherein at least one of the plurality of interchangeable cutting heads further comprises an angled distal end and a cutting window oriented at an angle pointing toward the angled distal end.

18. The surgical cutting tool of claim 13 wherein at least one of the plurality of interchangeable cutting heads further comprises a flat distal end and a cutting window positioned proximal to the flat distal end.

19. The surgical cutting tool of claim 13 wherein at least one of the plurality of interchangeable cutting heads further comprises an angled distal end that extends beyond a diameter of the cannula and a cutting window positioned proximal to the angled distal end.

20. A method of using a surgical cutting tool, wherein the surgical cutting tool comprises a body further comprising a proximal end and a distal end, a cannula rotatably extending from the distal end of the body, the cannula having a proximal end and a distal end, a cutting head removably coupled to the distal end of the cannula, the cutting head further comprising a distal tip and a cutting window, a hollow shaft movably positioned inside the cannula, the hollow shaft further comprising a blade, a suction connector in fluid communication with the body, the suction connector being configured for connection to a suction source, a suction control coupled to the body and movable between an open position to reduce suction through the hollow shaft and the cutting window and a closed position to increase suction through the hollow shaft and the cutting window; and an actuator coupled to the hollow shaft for moving the blade of the hollow shaft relative to the cutting window of the cutting head, the method comprising:

inserting the cannula into a patient to a desired surgical site;

orienting the cutting window to the tissue to be cut;

manipulating the actuator to move the shaft blade across the cutting window to sever tissue extending into the cutting window; and withdrawing the cannula from a patient.

21. The method of using a surgical cutting tool of claim 20 wherein the step of inserting the cannula further comprises moving the suction control to the open position to reduce suction through the hollow shaft and the cutting window.

22. The method of using surgical cutting tool of claim 21 wherein after inserting the cannula into a patient, the method further comprises the step of moving the suction control to the closed position to increase suction through the hollow shaft and the cutting window to draw tissue into the cutting window.

* * * * *